US008834697B2

United States Patent
Kaji

(10) Patent No.: US 8,834,697 B2
(45) Date of Patent: Sep. 16, 2014

(54) ELECTROPHORESIS APPARATUS AND A METHOD FOR ELECTROPHORESIS

(75) Inventor: Toru Kaji, Kyoto (JP)

(73) Assignee: Shimadzu Corporation, Kyoto (JP)

(*) Notice: Subject to any disclaimer, the term of this patent is extended or adjusted under 35 U.S.C. 154(b) by 663 days.

(21) Appl. No.: 12/597,087

(22) PCT Filed: Apr. 25, 2007

(86) PCT No.: PCT/JP2007/000454
§ 371 (c)(1),
(2), (4) Date: Oct. 22, 2009

(87) PCT Pub. No.: WO2008/136057
PCT Pub. Date: Nov. 13, 2008

(65) Prior Publication Data
US 2010/0116661 A1 May 13, 2010

(51) Int. Cl.
*G01N 27/447* (2006.01)
*G01N 35/00* (2006.01)

(52) U.S. Cl.
CPC .... *G01N 27/447* (2013.01); *G01N 2035/00158* (2013.01)
USPC ........... 204/456; 204/604; 204/453; 204/606; 435/287.1; 422/82.01; 422/68.1

(58) Field of Classification Search
USPC ......... 204/600–643, 453, 457, 456; 422/68.1, 422/82.01; 435/287.1
See application file for complete search history.

(56) References Cited

U.S. PATENT DOCUMENTS 5,635,050 A 6/1997 Pentoney, Jr. et al.
6,132,579 A * 10/2000 Edwards et al. .............. 204/451
(Continued)

FOREIGN PATENT DOCUMENTS

| JP | 2001-296275 A | 10/2001 |
| JP | 2005-274512 A | 10/2005 |
| JP | 2005-331411 | * 12/2005 |
| JP | 2006-250622 A | 9/2006 |

OTHER PUBLICATIONS

Machine translation of JP 2005-331411.*

(Continued)

Primary Examiner — Jennifer Dieterle
(74) Attorney, Agent, or Firm — Sughrue Mion, PLLC

(57) ABSTRACT

A channel (12) is formed inside a transparent substrate (11), and the two ends are respectively connected to a sample inlet (13) and a separation medium filling port (14) both open to outside, and a sample outlet (15) which is open to outside is provided on the channel (12). The portion between the sample inlet (13) and the sample outlet (15) is a separation channel portion (12a), and the portion between the sample outlet (15) and the separation medium filling port (14) is a separation medium introduction channel portion (12b). A separation medium supplier is connected to the separation medium filling port (14) and the separation medium introduction channel portion (12b) is filled with a separation medium. Then a sample is dropped to the sample inlet (13), with the sample medium supplier still connected, to introduce the sample to the separation channel portion (12a). And then, buffer liquid is poured in buffer reservoirs (16) and (17) and a migration voltage is applied to perform a migration analysis. Since an analysis can be repeatedly performed with the sample medium supplier kept connected, it is not necessary to disconnect the supplier from the electrophoretic chip each time a migration is performed.

6 Claims, 3 Drawing Sheets

(56) References Cited

U.S. PATENT DOCUMENTS

| | | | |
|---|---|---|---|
| 2002/0104759 A1* | 8/2002 | Backhouse | 204/453 |
| 2002/0144907 A1* | 10/2002 | Yamamoto | 204/453 |
| 2006/0049051 A1* | 3/2006 | Yeung et al. | 204/450 |
| 2006/0213775 A1* | 9/2006 | Ohashi et al. | 204/601 |

OTHER PUBLICATIONS

Written Opinion of the International Searching Authority dated May 29, 2007, issued in corresponding International application No. PCT/JP2007/000454.

* cited by examiner

ELECTROPHORESIS APPARATUS AND A METHOD FOR ELECTROPHORESIS

TECHNICAL FIELD

The present invention relates to an electrophoretic chip which is a device suitable for use in the fields of mainly biochemistry, molecular biology, clinical medicine, and in particular, analysis of DNA and protein, or other fields. The present invention also relates to a method of the electrophoresis using the electrophoretic chip.

BACKGROUND ART

Capillary electrophoresis (CE) is a method suitable for the analysis of a biological sample such as peptide, protein, DNA, and sugar. It is also suitable for the optical resolution, isotope separation, and other processes, in which components having similar structures are separated. It is widely used in the application of clinical medicine, pharmaceutical drugs, monitoring of environmental substances, etc. In particular, the apparatus (microchip electrophoresis apparatus) using a microchip in which microchannels are formed by using the photolithography technique and other techniques has come to be much used in recent years for the analysis of DNA and other applications because it is very easy to handle (for example, refer to Non-Patent Document 1).

The microchip electrophoresis apparatus uses, in order to separate a sample into components, an electrophoretic chip in which separation channels are formed on a substrate such as a glass plate, silica glass plate, or other plate. In the electrophoretic chip, as disclosed in Patent Document 1 for example, separation channels for electrophoresis are formed inside a plate substrate made with glass or other materials, and the channels are open at both ends on the surfaces of the substrate. The opening at one end side is a sample inlet and the opening at the other end side is a sample outlet.

In performing an analysis, a separation medium supplier is first connected to one opening, and a separation medium such as a gel is filled in the separation channels by applying a pressure by a syringe included in the apparatus. Then, a sample is injected from a sample reservoir provided at the sample inlet, and after that, a buffer (migration liquid) is injected to the reservoir and a predetermined migration voltage is applied between the ends of the channels to electrophorese the sample from the sample inlet toward the sample outlet. With the electrophoresis, the components in the sample are separated in the longitudinal direction of the separation channel owing to the separation medium, and the components that come out with different times are sequentially detected by a detector placed at the sample outlet of the separation channel, for example.

In the aforementioned configuration, when the voltage is applied between the electrodes after the buffer is filled in the reservoir, the separation medium supplier obstructs the application of the voltage. Thus it is necessary to remove (or set offline) the separation medium supplier from the electrophoretic chip. Providing such a movement mechanism complicates the apparatus and increases its cost.

In addition, in order to frequently connect and disconnect the separation medium supplier to and from the electrophoretic chip, the end of the injection nozzle of the supplier needs to be sufficiently larger than the opening of the electrophoretic chip so that the nozzle is assuredly connected to the opening even when a displacement occurs. This brings about a large dead volume between the end of the nozzle and the opening, which requires an additional amount of separation medium, and increases the analysis cost.

When the injection nozzle of the separation medium supplier is disconnected from the electrophoretic chip, the separation medium remaining on the tip of the nozzle dries out. When the separation medium is next injected, an extra amount of separation medium is required to be injected in order to remove the dried separation medium. In this respect, also, an additional amount of separation medium is necessary, which increases the analysis cost.

Furthermore, when the injection nozzle that has been disconnected from the electrophoretic chip is connected to the opening, and a separation medium is injected, bubbles may be introduced and enter the separation channel. This necessitates an additional amount of the separation medium in order to expel the bubbles out of the separation channel.

What is more, every time the separation medium filling operation is made, the buffer in the buffer storage tank (buffer reservoir) provided at the sample inlet or at the sample outlet must be removed. This increases the use of the buffer, which may increase the analysis cost.

In one known configuration of an electrophoresis apparatus using not a microchip but a capillary tube, a separation medium introduction channel with a separation medium supplier provided at one end is connected to the capillary tube (separation channel) via a connector so an electrophoresis can be performed without removing the separation medium supplier (for example, refer to Patent Document 2). However, such a configuration has a disadvantage in that, since a high pressure is applied to the joint of the separation channel and the separation medium introduction channel when injecting the separation medium or at other processes, a high-pressure seal is necessary to resist such a pressure.

[Patent Document 1] Japanese Unexamined Patent Application Publication No. 2006-250622
[Patent Document 2] U.S. Pat. No. 5,635,050
[Non-Patent Document 1] Arai and six other authors, "Microchip electrophoresis apparatus MCE-2010 no Kihatsu to sono Oyo," [online], March 2003, SHIMADZU CORPORATION, Internet <http://www.shimadzu-biotech.jp/datahall/mce/sr58-101.pdf>, [Mar. 20, 2007]

DISCLOSURE OF THE INVENTION

Problems to be Solved by the Invention

The present invention has been achieved to solve the aforementioned problems, and the main objective thereof is to provide an electrophoretic chip, and a method of the electrophoresis, that simplifies the configuration of the separation medium supplier for filling the channel with a separation medium, and also the configuration of the apparatus accompanying the separation medium supplier, to decrease the cost of the apparatus.

Another objective of the present invention is to provide an electrophoretic chip, and a method of the electrophoresis, that lowers the analysis cost by suppressing the wasteful use of the separation medium and buffer.

Means for Solving the Problems

To solve the previously-described problem, the present invention provides an electrophoretic chip including:
 a) a channel formed inside a plate unit;
 b) a first opening and a second opening, respectively connected to the two ends of the channel, and each being open to outside; and c) a third opening provided midway on the channel, the third opening being open to outside,
where, among the channel, the portion between the first opening and the third opening is made to be a separation channel portion for electrophoresis, and the portion between the third opening and the second opening is made to be a separation medium introduction channel portion for transporting a separation medium injected from the second opening to the separation channel portion.

In the separation analysis using the electrophoretic chip according to the present invention, the second opening connected to one end of the channel is assigned exclusively for injecting the separation medium. For other openings, for example, the first opening connected to the other end is assigned to the sample inlet, and the third opening provided midway on the channel is assigned to the sample outlet. Then, a separation medium supplier is connected to the second opening so that the separation medium can be injected to the channel from this opening.

Effect of the Invention

As previously described, in the electrophoretic chip according to the present invention, the opening for injecting a separation medium to the channel is provided separately from the sample inlet and the sample outlet. Therefore, in the method for electrophoresis using this electrophoretic chip, with the separation medium supplier for injecting the separation medium being connected to the second opening, electrophoresis in the separation channel portion can be performed by applying a voltage between the first opening and the third opening. That is, after filling the channel with the separation medium, the separation medium supplier is not necessary to be disconnected from the second opening both at the times of injecting a sample into the separation channel and of performing electrophoresis. In other words, it is possible to realize the state ("online state") in which the separation medium supplier is always connected to the channel.

This brings about the following advantages to the electrophoretic chip according to the present invention, compared to the conventional configurations in which the separation medium supplier is required to be disconnected and substantially moved from the electrophoretic chip every time the injection of a sample and electrophoresis are performed.

That is, there is no need of providing a drive mechanism for moving the separation medium supplier by a substantial distance and with a high positional accuracy, so that the electrophoresis apparatus using this electrophoretic chip is simplified and the cost of the apparatus can be reduced. In addition, since the separation medium supplier can be fixed to the electrophoretic chip, a high-precision seal mechanism indispensable to connecting and disconnecting them is unnecessary, and an inexpensive seal mechanism can be used to reduce the cost of the apparatus.

Since the displacement in connecting the separation medium supplier to the electrophoretic chip is of no regard, the dead volume between the end of the injection nozzle and the opening can be decreased. Moreover, the separation medium supplier can be kept connected to the electrophoretic chip while performing electrophoresis, so that the separation medium may not be dehydrated and bubbles may not be introduced in it. These all minimize the waste of separation medium, and the use of the separation medium can be decreased to reduce the analysis cost.

In the electrophoretic chip according to the present invention, the separation channel portion and the separation medium introduction channel portion are connected without disposing any element such as a connector. Therefore, the channels need not be connected with a high-pressure seal which was necessary for a previously described capillary electrophoresis apparatus.

In a method for electrophoresis using the electrophoretic chip according to the present invention, the separation medium is filled in the separation channel portion as follows. With the third opening opened, the separation medium is injected from the second opening by the separation medium supplier to fill the separation medium introduction channel portion with the separation medium. Then, with the third opening closed, the separation medium is injected from the second opening by the separation medium supplier to introduce the separation medium in the separation channel portion.

When the separation medium is injected from the second opening with the third opening opened, the separation medium fills the separation medium introduction channel portion and overflows from the third opening. This completely flushes out the separation medium of the previous analysis remaining in the third opening. Next, the third opening is closed and the separation medium is injected from the second opening. Then, the separation medium that filled the separation medium introduction channel portion is pushed and enters the separation channel portion, filling the separation channel portion together with the added separation medium. If the separation medium of the previous analysis remains in the separation channel portion, this old separation medium is pushed out from the first opening. Thereby, the separation medium in the separation channel portion can be easily and completely replaced.

After that, the third opening is opened, a sample is put to the first opening, and a predetermined voltage is applied between the first opening and the third opening to introduce the sample to the separation channel portion. In addition, the sample is made to electrophorese by applying a predetermined migration voltage, and the sample components are separated, by the action of the separation medium, in the longitudinal direction of the separation channel portion, and are detected. For this detection, a fluorescence detector, conductometric detector, or other detectors can be used.

In the electrophoresis as just described, the third opening, which is close to the second opening to which the separation medium supplier is connected, may preferably be set at the ground potential. This brings a position of the channel between the first opening and the second opening to the ground potential, and the migration voltage develops between the position and the first opening. Therefore, a leakage current caused by this migration voltage does not flow to the second opening to which the separation medium supplier is connected. This prevents the apparatus from failing due to the leakage current, and assures a high safety.

In the method for electrophoresis according to the present invention, each of the first opening and the second opening may have a liquid reservoir, and a migration liquid may be stored in the liquid reservoir. The migration voltage can be applied between electrodes immersed in the migration liquid, and the electrophoresis may be repeatedly performed without changing the migration liquid in the liquid reservoir at the side of sample migration outlet.

That is, the migration liquid stored in the liquid reservoir at the side of sample outlet is not necessary to be removed in supplying the separation medium. Therefore, as long as the migration liquid has a buffer capacity (as long as an electrophoretic operation is possible), an analysis can be repeated without replacing the migration liquid. This can reduce the use of the migration liquid to migrate the analysis cost.

EXPLANATION OF NUMERALS

10 . . . Electrophoretic Chip
11 . . . Substrate
11a, 11b . . . Transparent Flat Plate
12 . . . Channel
12a . . . Separation Channel Portion
12b . . . Separation Medium Introduction Channel Portion
13 . . . Sample Inlet
14 . . . Separation Medium Filling Port
15 . . . Sample Outlet
16 . . . First Buffer Reservoir
17 . . . Second Buffer Reservoir
20 . . . Sample Injector
21 . . . Migration Voltage Applier
23 . . . Buffer Injector
24 . . . Separation Medium Supplier
241 . . . Syringe
242 . . . Separation Medium
243 . . . Plunger
244 . . . Nozzle
245 . . . Seal Unit
25 . . . Cleaning Unit
26 . . . Fluorescence Detector
27 . . . Data Processor
28 . . . Controller

BEST MODE FOR CARRYING OUT THE INVENTION

Figure 1:
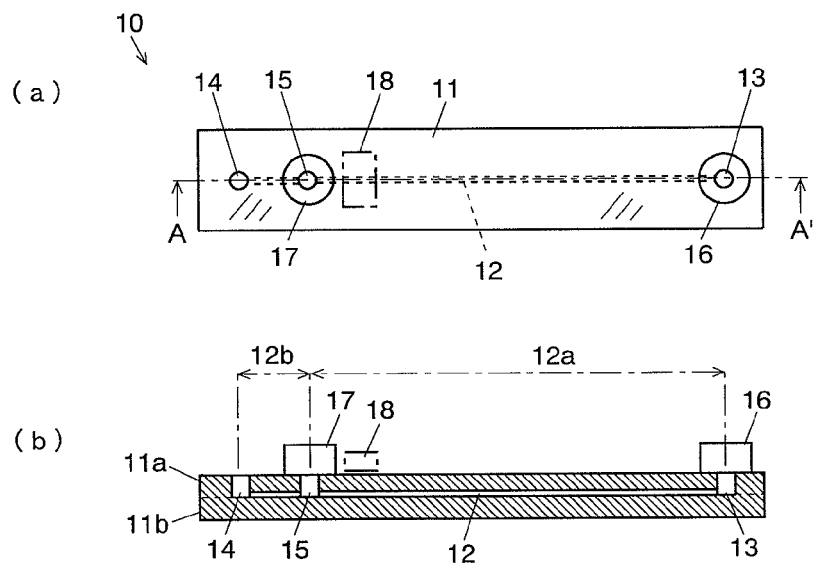
FIG. 1(a) is a top plain view of the electrophoretic chip according to an embodiment of the present invention.
FIG. 1(b) is a sectional view at line A-A' of the electrophoretic chip.

First, the structure of one embodiment of the electrophoretic chip according to the present invention will be described with reference to FIG. 1. FIG. 1(a) is a top plain view of the electrophoretic chip 10 according to the present embodiment, and FIG. 1(b) is a sectional view at line A-A' in FIG. 1(a).

The electrophoretic chip 10 has a substrate 11 having the shape of a long, flat parallelepiped and in which a pair of transparent flat plates 11a and 11b such as a glass plate, silica glass plate, or other plate are bonded. On the lower face of the upper transparent flat plate 11a, a straight line groove is formed, by etching for example. At both ends of the groove, cylindrical through-holes are bored, and at a position midway, but closer to one of the ends, on the groove, a third cylindrical through-hold is bored. The groove has a width of about 10 to 100 μm, and a depth of about 5 to 50 μm.

The pair of transparent flat plates 11a and 11b are bonded with the groove facing inside. Thereby, the open top of the groove facing downwards is covered by the upper surface of the lower transparent flat plate 11b, which forms a straight line channel 12 inside the substrate 1. The lower open tops of the three through-holes placed at both ends and at a midway of the channel 12 are covered by the upper surface of the transparent flat plate 11b. This forms three openings, at both ends and at a midway of the channel 12, on the upper surface of the substrate 11. In the present embodiment, in FIG. 1, the first opening is formed on the right end of the channel 12, the second opening on the left end thereof, and the third opening between them. The first opening is the sample inlet 13, the third opening is the sample outlet 15, and the second opening is the separation medium filling port 14.

Functionally, the channel 12 can be divided into two portions: a separation channel portion 12a spanning between the sample inlet 13 and the sample outlet 15, and a separation medium introduction channel portion 12b spanning between the sample inlet 15 and the sample medium filling port 14. On the sample inlet 13, a first buffer reservoir 16 for storing a buffer (migration liquid) is provided, and on the sample outlet 15, likewise, a second buffer reservoir 17 for storing a buffer is provided. At the position of numeral 18 in FIG. 1, a detector, which will be described later, for detecting the sample components separated in the separation channel portion 12a is placed.

Figure 2:
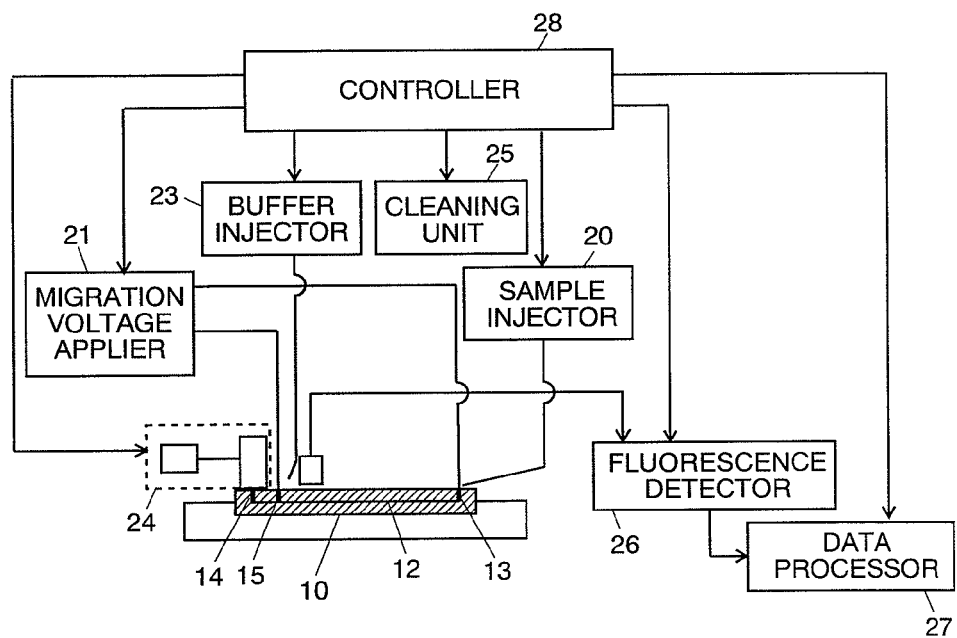
FIG. 2 is a configuration diagram of the main portion of the electrophoretic analysis system using the electrophoretic chip of the present embodiment.

FIG. 2 is a configuration diagram of the main portion of the entire electrophoretic analysis system using the electrophoretic chip 10 of the present embodiment. A sample injector 20 is for dropping the sample to be analyzed to the sample inlet 13 of the electrophoretic chip 10. A migration voltage applier 21 includes a pair of electrodes and is used to apply a predetermined migration voltage between both ends of the separation channel portion 12a. A buffer injector 23 is for injecting a buffer (or migration liquid) to the first and second buffer reservoirs 16 and 17. A separation medium supplier 24 is for injecting a separation medium such as a migration polymer from the sample medium filling port 14. A cleaning unit 25 is for cleaning the sample inlet 13, the buffer reservoirs 16 and 17, etc. A fluorescence detector 26 includes an excitation light irradiator and a light receiver which are placed at the position of numeral 18 in FIG. 1, and sequentially detects the sample components separated in the separation channel portion 12a over time to generate a detection signal for each of them. A data processor 27 receives the detection signals and performs predetermined data processings. A controller 28 systematically controls the aforementioned units to allow an automatic analysis. The data processing function included in the data processor 27 can be realized by running dedicated software on a general-purpose computer.

Figure 3:
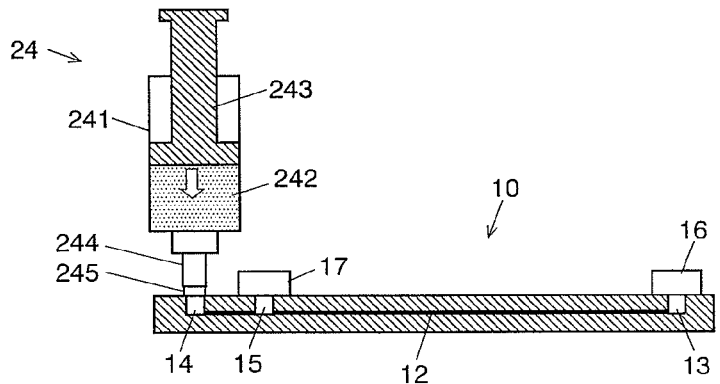
FIG. 3 is a schematic diagram illustrating the state in which a separation medium supplier is attached to the electrophoretic chip of the present embodiment.

FIG. 3 is a schematic diagram illustrating the state in which the separation medium supplier 24 is attached to the electrophoretic chip 10. In the separation medium supplier 24, a separation medium 242 held in a syringe 241 is pressed down with the plunger 243 to extrude the separation medium 242 from a nozzle 244. At the end of the nozzle 244, a seal unit 245 is provided in order to attach more firmly to the upper surface of the substrate 11 of the electrophoretic chip 10.

Figure 4:
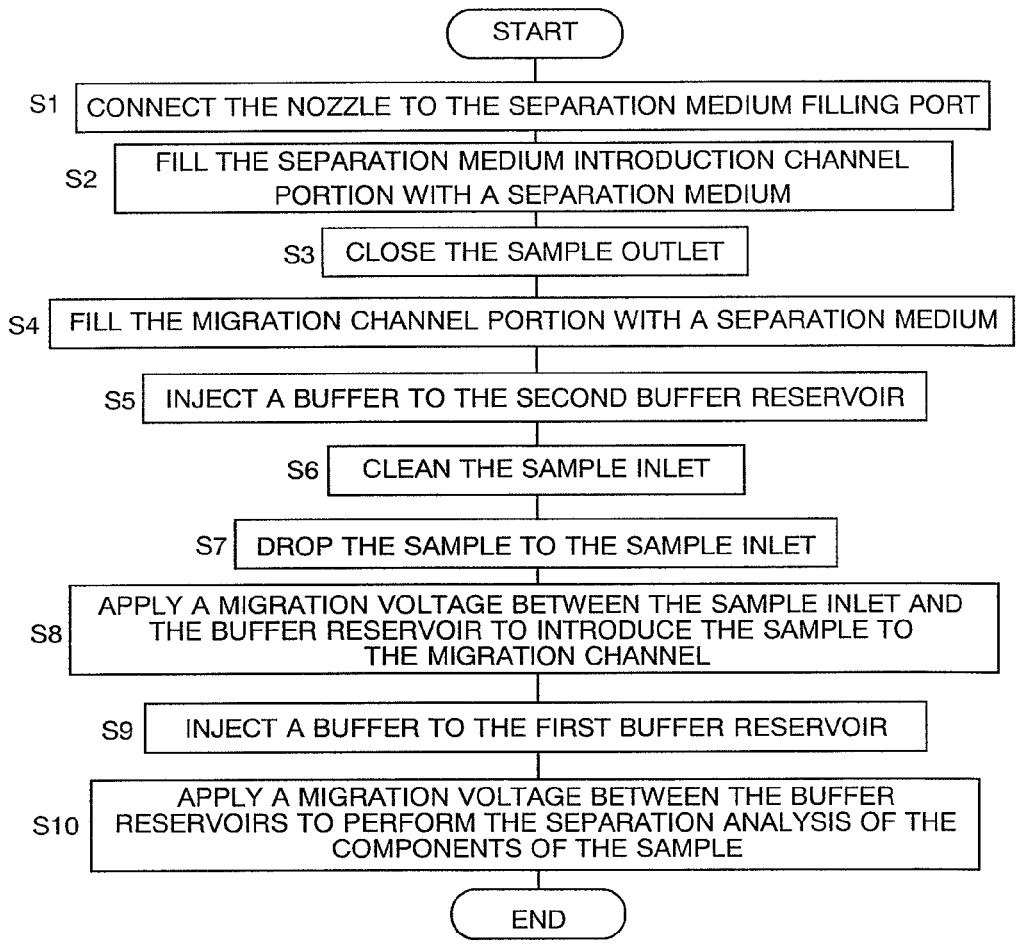
FIG. 4 is a flowchart illustrating an example of the analysis procedure in the electrophoretic analysis system of FIG. 2.

Next, an example of the analysis procedure in the aforementioned analysis system is described in accordance with the flowchart of FIG. 4. First, as illustrated in FIG. 3, the separation medium supplier 24 is fixed in such a manner that the end of the nozzle 244 is firmly attached to the separation medium filling port 14 of the electrophoretic chip 10 (Step S1). Next, the plunger 243 of the separation medium supplier 24 is pressed down by a predetermined distance to inject the separation medium extruded from the nozzle 244 to the separation medium introduction channel portion 12b through the separation medium filling port 14 to fill the separation medium introduction channel portion 12b (Step S2). Since the sample outlet 15 is open at this time, after the separation medium fills the separation medium introduction channel portion 12b, a portion of the separation medium overflows the sample outlet 15. After that, the sample outlet 15 is closed with a predetermined blocking unit (Step S3), and the plunger 243 of the separation medium supplier 24 is pressed down to fill the separation channel portion 12a with the separation medium (Step S4). Then, an appropriate amount of buffer is injected to the second buffer reservoir 17 by the buffer injector 23 to be stored (Step S5).

Subsequently, the sample inlet 13 is cleaned by the cleaning unit 25 in order to remove the separation medium that has overflowed the sample inlet 13 (Step S6), and an appropriate amount of sample is dropped to the sample inlet 13 by the sample injector 20 (Step S7). Then, the migration voltage applier 21 immerses each of a pair of electrodes in the buffer in the second buffer reservoir 17 and in the sample in the sample inlet 13, and applies a predetermined voltage (Step S8). This introduces the sample to the separation channel portion 12a.

Then, the buffer is injected to the first buffer reservoir 16 by the buffer injector 23, whereby it is stored there (Step S9). At this time, the buffer that has been injected in Step S7 is stored in the second buffer reservoir 17. Then, by the migration voltage applier 21, a predetermined migration voltage is applied between the electrode immersed in the buffer in the first buffer reservoir 16 and the electrode immersed in the buffer in the second buffer reservoir 17. By the electric field formed by this migration voltage, the sample that have been previously introduced around the entrance of the separation channel portion 12a is made to migrate toward the sample outlet 15. In this migration, due to the interaction between the separation medium that fills the separation channel portion 12a and respective components of the sample, the components are separated in the longitudinal direction of the separation channel portion 12a.

When the sample components thus separated pass the measurement position where the excitation light irradiator and the light receiver of the fluorescence detector 26 are present, the difference in the fluorescence properties is detected by the fluorescence detector 26, and the detection signal indicating the difference is obtained (Step S10). In the data processor 27, based on the data obtained by converting the detection signal into digital values, an electropherogram with respect to the migration time is created.

When a migration analysis on another samples is performed subsequent to the aforementioned analysis, the buffer remaining in the first buffer reservoir 16 is sucked and the reservoir 16 is cleaned. Then, the process returns to Step S2 and the cycle of the next analysis is performed. In the subsequent analysis, when the separation medium is thrusted to the separation medium introduction channel portion 12b and the separation channel portion 12a by the separation medium supplier 24, the separation medium that was used in the previous analysis is expelled from the channel portions 12a and 12b, and the separation medium is replaced. Thereby, the contamination is avoided.

Before proceeding to the next analysis, the buffer in the second buffer reservoir 17 may also be sucked. However, since this buffer is (or was) not drawn to the channel 12, it is not necessary to be replaced as long as it has the buffer capacity, i.e. as long as it can form the electric field for migration by the application of voltage. Therefore, even when the migration analysis is repeated, the buffer in the second buffer reservoir 17 needs not be removed or cleaned, whereby the running cost of the analysis can be reduced.

As previously described, in the electrophoretic analysis using the electrophoretic chip of the present embodiment, a migration analysis can be performed with the separation medium supplier 24 attached to the electrophoretic chip. And the migration analysis can be performed repeatedly.

Figure 5:
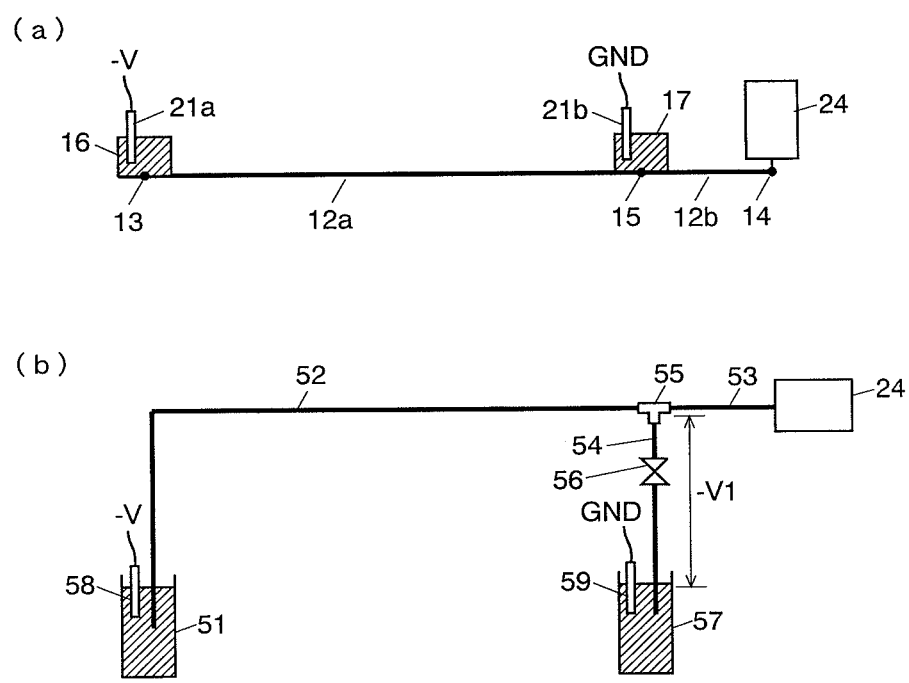
FIG. 5 are schematic diagrams for explaining the difference between the electrophoretic chip according to the present embodiment and a conventional capillary electrophoresis apparatus.

It may be feared that, when a migration voltage is applied with the separation medium supplier 24 attached, a leak current caused by the voltage may flow into the separation medium supplier 24, and a safety hazard might occur. In addition, this may cause the breakdown of the separation medium supplier 24. With the configuration of the present embodiment, such risks due to the leakage current can be reduced, which is explained with reference to FIG. 5. FIG. 5(a) is an explanation diagram in the case where a migration voltage is applied in the configuration of the present embodiment, and FIG. 5(b) is an explanation diagram for the capillary electrophoresis apparatus with the similar configuration using a capillary tube.

In the configuration of FIG. 5(b), an end of the capillary tube 52 as a separation channel is connected to the buffer storage tank 51, and the other end is connected through a T-joint 55 to an end of another capillary tube 53 for introducing separation medium and to an end of a third capillary tube 54 for discharging sample. The other end of the capillary tube 54 for sample discharge is connected to a buffer storage tank 57, and a valve 56 is provided on the capillary tube 54. To the other end of the capillary tube 53 for introducing separation medium, the separation medium supplier 24 is connected. In each of the buffer storage tanks 51 and 57, a buffer is stored, and electrodes 58 and 59 for applying a migration voltage are provided to be immersed in the buffer.

With this configuration, the electrode 59 is set at the ground potential (GND) and a negative high voltage (−V) is applied to the electrode 58 to apply a migration voltage between the two ends of the capillary tube 52. Since, a voltage drop occurs between the two ends of the capillary tube 54 for sample discharge, a negative voltage (−V1) is present at the T-joint 55. When the voltage V is 1000[V], for example, and supposing that 1/100 of the voltage is applied to the T-joint 55, the voltage V1 is 10[V]. Though the separation medium supplier 24 is set at the ground potential, a leak current corresponding to the voltage difference of 10[V] and the electric resistance of the capillary tube 53 flows into the separation medium supplier 24.

On the other hand, when the electrophoretic chip of the present embodiment is used, as illustrated in FIG. 5(a), the migration voltage is applied between the electrode 21a immersed in the buffer in the first buffer reservoir 16 and the electrode 21b immersed in the buffer in the second buffer reservoir 17. When the electrode 21b is set to the ground potential (GND), the electric potential at the connection point of the separation channel portion 12a and the separation medium introduction channel portion 12b is substantially zero. Therefore, substantially zero voltage is present between the two ends of the separation medium introduction channel portion 12b, and substantially zero current flows into the separation medium supplier 24. As just described, in the migration analysis using the electrophoretic chip according to the present embodiment, even if a migration voltage is applied while the separation medium supplier 24 is connected, the leak current can be avoided to flow into the separation medium supplier 24.

Since the embodiment described thus far is merely an example of the present invention, and it is evident that any modification, adjustment or addition properly made within the spirit of the preset invention is also covered within the scope of the claims of this patent application. For example, although one channel 12 is provided in the substrate 11 in the aforementioned embodiment, a plurality of parallel channels can be provided for example.

The invention claimed is:

1. A method for electrophoresis using an electrophoretic chip including a channel formed inside a plate unit; a first opening and a second opening, respectively connected to the two ends of the channel, and each being open to outside; and a third opening provided midway on the channel, the third opening being open to outside, the method comprising:
providing electrophoresis in the channel, at a separation channel portion between the first opening and the third opening,
transporting a separation medium injected from the second opening to the separation channel portion at a separation medium introduction channel portion between the third opening and the second opening,
injecting a sample from the first opening to the separation channel portion,
injecting the separation medium by a separation medium supplier being connected to the second opening, while applying a voltage between the first opening and the third opening to perform electrophoresis in the separation channel portion, and
discharging the sample made to migrate from the first opening toward the third opening, through the third opening.

2. The method for electrophoresis according to claim 1, further comprising:
injecting a separation medium from the second opening by the separation medium supplier with the third opening opened to fill the separation medium introduction channel portion with the separation medium, and
injecting a separation medium from the second opening by the separation medium supplier with the third opening closed to introduce the separation medium in the separation channel portion.

3. The method for electrophoresis according to claim 1, wherein the third opening is set at a ground potential in the electrophoresis.

4. The method for electrophoresis according to claim 1, further comprising:
providing a liquid reservoir for each of the first opening and the third opening;
storing migration liquid in each of the liquid reservoir;
applying a migration voltage between electrodes immersed in the migration liquid of the liquid reservoirs; and
performing the electrophoresis plural times without changing the migration liquid in the liquid reservoir on a side of a sample outlet with respect to a migration.

5. An electrophoresis apparatus for electrophoresing a sample in a separation channel filled with a separation medium to separate the sample into components comprising:
a) a sample injector configured to inject the sample;
b) an electrophoretic chip including: a channel formed inside a plate unit; a first opening to which the sample injector is connected and a second opening, respectively connected to the two ends of the channel, and each being open to outside; and a third opening provided midway on the channel, the third opening being open to outside, where, among the channel, the first opening is made to be a sample inlet, the third opening is configured to be a sample outlet, a portion between the first opening and the third opening is configured to be a separation channel portion for electrophoresis, and a portion between the third opening and the second opening is configured to be a separation medium introduction channel portion for transporting a separation medium injected from the second opening to the separation channel portion;
c) a separation medium supplier connected to the second opening configured to inject the separation medium into the separation channel portion through the separation medium introduction channel portion; and
d) a migration voltage applier configured to apply a predetermined voltage between the first opening and the third opening in order to perform an electrophoresis in the separation channel portion with the separation medium supplier connected to the second opening.

6. An electrophoresis apparatus for electrophoresing a sample in a separation channel filled with a separation medium to separate the sample into components comprising:
a) a sample injector configured to inject the sample;
b) an electrophoretic chip including: a channel formed inside a plate unit; a first opening to which the sample injector is connected and a second opening, respectively connected to the two ends of the channel, and each being open to outside; and a third opening provided midway on the channel, the third opening being open to outside, where, among the channel, the first opening is configured to be a sample inlet, the third opening is configured to be a sample outlet, a portion between the first opening and the third opening is configured to be a separation channel portion for electrophoresis, and a portion between the third opening and the second opening is configured to be a separation medium introduction channel portion for transporting a separation medium injected from the second opening to the separation channel portion;
c) a separation medium supplier connected to the second opening configured to inject the separation medium into the separation channel portion through the separation medium introduction channel portion; and
d) a migration voltage applier configured to apply a predetermined voltage between the first opening and the third opening in order to introduce the sample in the first opening in the separation channel and perform an electrophoresis in the separation channel portion with the separation medium supplier connected to the second opening.

* * * * *